United States Patent [19]
Cullinan

[11] Patent Number: 6,096,781
[45] Date of Patent: Aug. 1, 2000

[54] 2-ARYLBENZO[B]THIOPHENES USEFUL FOR THE TREATMENT OF ESTROGEN DEPRIVATION SYNDROME

[75] Inventor: George Joseph Cullinan, Trafalgar, Ind.

[73] Assignee: Eli Lilly and Company, Indianapolis, Ind.

[21] Appl. No.: 09/185,927

[22] Filed: Nov. 4, 1998

Related U.S. Application Data

[60] Provisional application No. 60/065,854, Nov. 14, 1997.
[51] Int. Cl.[7] .................................................... A61K 31/38
[52] U.S. Cl. ......................... 514/438; 514/446; 514/448
[58] Field of Search ................................. 514/438, 446, 514/448

[56] References Cited

U.S. PATENT DOCUMENTS

| | | | |
|---|---|---|---|
| 4,418,068 | 11/1983 | Jones | 424/267 |
| 4,588,484 | 5/1986 | Justice, Jr. et al. | 204/59 R |
| 5,389,670 | 2/1995 | Fontana | 514/443 |
| 5,391,557 | 2/1995 | Cullinan et al. | 514/324 |
| 5,393,763 | 2/1995 | Black et al. | 514/333 |
| 5,464,845 | 11/1995 | Black et al. | 514/326 |
| 5,488,058 | 1/1996 | Palkowitz | 514/324 |
| 5,492,922 | 2/1996 | Palkowitz | 514/324 |
| 5,510,357 | 4/1996 | Palkowitz | 514/324 |
| 5,514,703 | 5/1996 | Carlson et al. | 514/443 |
| 5,514,704 | 5/1996 | Carlson et al. | 514/443 |
| 5,532,382 | 7/1996 | Carlson et al. | 549/57 |
| 5,534,526 | 7/1996 | Cullinan et al. | 514/432 |
| 5,641,790 | 6/1997 | Draper | 514/333 |
| 5,646,137 | 7/1997 | Black et al. | 514/171 |
| 5,670,514 | 9/1997 | Audia et al. | 514/298 |
| 5,686,476 | 11/1997 | May | 514/324 |
| 5,723,474 | 3/1998 | Palkowitz | 514/324 |
| 5,731,342 | 3/1998 | Cullinan et al. | 514/443 |
| 5,747,510 | 5/1998 | Draper | 514/333 |
| 5,760,061 | 6/1998 | Fontana | 514/324 |
| 5,811,120 | 9/1998 | Gibson et al. | 424/464 |
| 5,972,383 | 10/1999 | Gibson et al. | 424/464 |

FOREIGN PATENT DOCUMENTS

| | | |
|---|---|---|
| 0729 956 A1 | 2/1996 | European Pat. Off. . |
| 0747376 A1 | 5/1996 | European Pat. Off. . |
| WO 970 1549 A1 | 6/1996 | WIPO . |
| WO 98/45287 | 4/1998 | WIPO . |
| WO 99/25706 | 11/1998 | WIPO . |
| WO 99/25707 | 11/1998 | WIPO . |

OTHER PUBLICATIONS

Draper et al., "effects of Raloxifene (LY139481 HCl) on Biochemical Markers of Bone and Lipid Metabolism Healthy Postmemopausal Women", Hong Kong, Fourth Int'l Symp. on Osteoporosis, Mar. 29, 1993.

Bryant et al., "Protection fro Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist",Am Soc. Bone & Min. Res., Tampa, Sep. 18–22, 1993.

Frolik et al., "In Vivo and In Vitro Metabolism of Raloxifene", Am.Soc. Bone & Min. Res., Tampa Sep. 18–22, 1993.

Glasebrook et al., "Multiple Binding Sites for the Antiestrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone & Min. Res., Tampa, Sep. 18–22, 1993.

Yang et al., "Raloxifene and Anti–Estrogen, Simulates the Effects of Estrogen in Inhibiting Bone Resorption Through Regulating TCGB–3 Expression in Bone;" Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series; "The Endocrine Society, Abstract 1982.

Black et al., Uterine Bioassay of Tamoxifen, Trioxifene, and New Estrogen Antagonist (LY117018) in Rats and Mice, Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109; 1981, 987–989.

Black, L.J. "Biological Actions and Binding Properties of a New Estrogen Antagosist LY117018," In: Hormone Antagonists, 129–82, 1982, (M.K. Agarwal ed.) Walter de Gruyter and Co., Berlin New York.

(List continued on next page.)

Primary Examiner—Theodore J. Criares
Assistant Examiner—Jennifer Kim
Attorney, Agent, or Firm—William R. Boudreaux; James J. Sales

[57] ABSTRACT

This invention provides methods which are useful for the inhibition of the various medical conditions associated with estrogen deprivation syndrome including osteoporosis and hyperlipidemia utilizing compounds of formula I:

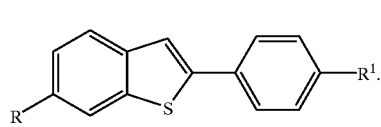

11 Claims, No Drawings

OTHER PUBLICATIONS

Black, et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New Benzothiophene Derived Antiestrogen, Life Sciences, 32:1983, 1031–1036.

Black et al., The Relationship of the Antiestrogenic Efficacy of LY156758 too its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22:1979, 962–966.

Black et al., Antiestrogens 2, Structure Activity Studies in a Series of 3–Aroyl–2–arylbenzo[b]thiophene Derivatives Leading to [6–Hydroxy–2–(4–hydroxyphenyl)benzo[b]thien–3–yl] [4–[2–(1–piperidinyl)ethoxy]–phenyl]methanone Hydrochloride (LY156758), a Remarkably Effective Estrogen Antagonist with Only Minimal Intrinsic Estrogenicity, J. Med.Chem. 27(8), 1984, 1057–166.

Health News Daily, vol. 9, No. 239, p. 1—Dec. 11, 1997.

Palkowitz, et al., Discovery and Synthesis of [6–Hydroxy–3–[4–[2–(1–piperdinyl)ethoxy]phenoxy]–2–(4 hydrooxyphenyl)]benzo[b]thiophene: A Novel, Highly Potent, Selective Estrogen Receptor Modulator, J. Med. Chem., 40(10), 1407–1416 (1997).

Capozzi, et al., Phthalimidesulfenyl Chloride; Part VII: Synthesis of 2–Substituted 3–Chlorobenzo[b]thio–[jemes amd Related Heteroaromatics, Synthesis, (5) 521–525 (1994).

Khovidhunkit, et al., "Clinical Effects of Raloxifene Hydrochloride in Women", Ann Intern Med, 130:431–9 (1999).

Delmas et al., Effects of Raloxifene on Bone Mineral Density, Serum Cholesterol Concentrations, and Uterine Endometrium in Postmenopausal Women, N. Engl J. Med., 337:1641–7 (1997).

Walsh, et al., "Effects of Raloxifene on Serum Lipids and Coagulation Factors in Healthy Postmenopausal Women", JAMA 279:1445–51 (1998).

Cummings, et al., "The Effect of Raloxcifene on Risk of Breast Cancer in Postmenopausal Women" JAMA, 281:2189–97 (1999).

Ettinger, et al., "Reduction of Vertebral Fracture Risk in Postmenopausal Women with Osteoporosis Treated with Raloxifene: Results from a 3–year randomized clinical trial" J. Am Med Assoc. 282:637–45 (1999).

Nickelsen, et al., "Raloxifene Hydrochloride, a Selective Estrogen Receptor Modulator: Safety Assessment of Effects on Cognitive Function and Mood in Postmenopausal Women" Psychoneuroendocrinology, 24:115–28 (1999).

2-ARYLBENZO[B]THIOPHENES USEFUL FOR THE TREATMENT OF ESTROGEN DEPRIVATION SYNDROME

This application claims the benefit of U.S. Provisional Application Ser. No. 60/065,854, filed Nov. 14, 1997.

FIELD OF THE INVENTION

This invention relates to the fields of pharmaceutical and organic chemistry and provides 2-arylbenzo[b]thiophenes which are useful for the inhibition of the various estrogen deficient conditions.

BACKGROUND OF THE INVENTION

"Estrogen deprivation syndrome" is a term used to describe various pathological conditions which frequently affect women who have insufficient levels of the hormone estrogen. The most common cause of estrogen deprivation in women is the natural cessation of menses with age, i.e., menopause. Additionally, non-natural circumstances including surgical ovariectomy, chemotherapy causing the cessation of hormone production or pharmacologic action, and the like, may induce estrogen deprivation. Although numerous pathologies are contemplated by the use of this term, two major effects of estrogen deprivation syndrome are the source of the greatest long-term medical concern: osteoporosis and cardiovascular effects, especially hyperlipidemia.

Osteoporosis describes a group of diseases which arise from diverse etiologies, but are all characterized by the net loss of bone mass per unit volume. The consequence of this loss of bone mass is the failure of the skeleton to provide adequate structural support for the body i.e. bone fracture. One of the most common types of osteoporosis is that associated with menopause. Most women lose from about 20% to about 60% of the bone mass in the trabecular compartment of the bone within 3 to 6 years after the cessation of menses. This rapid loss is generally associated with an overall increase of the bone resorption and bone formation cycle where the resorptive cycle is more dominant. The obvious result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is attributed to hip fractures in elderly women. A large percentage of this mortality rate can be directly associated with post- menopausal osteoporosis.

Throughout pre-menopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

Although estrogen replacement therapy is often prescribed for the estrogen deprivation syndrome, it suffers from poor patient compliance as many women object to some of the side-effects and the inconvenience of the pharmaceutical forms of the medication. For example, 17-β-estradiol is often administered via a transdermal patch, due to its poor oral absorption. As a result, a majority of women cease taking estrogen within the first year of beginning estrogen replacement therapy.

Compounds of formula I:

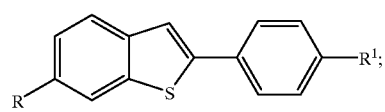

where:
R and $R^1$ are independently hydrogen, hydroxy, $C_1$–$C_6$ alkoxy, $OCH_2Ar$, $OCO(C_1$–$C_6$ alkyl), OCOAr; and
Ar is phenyl or substituted phenyl;
are known as chemical intermediates to oral pharmaceutical agents, e.g. raloxifene hydrochloride.

The present invention concerns the discovery of utilities newly attributed to compounds of formula I, namely, that they are agents useful in inhibiting estrogen deprivation syndrome.

SUMMARY OF THE INVENTION

The current invention provides methods for inhibiting estrogen deprivation syndrome in mammals which includes administering to a mammal in need thereof an effective amount of a compound of formula I:

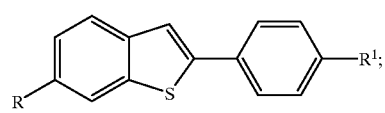

where:
R and $R^1$ are independently hydrogen, hydroxy, $C_1$–$C_6$ alkoxy, $OCH_2Ar$, $OCO(C_1$–$C_6$ alkyl), OCOAr; and
Ar is phenyl or substituted phenyl; or a solvate thereof.

Additionally, the current invention provides methods for inhibiting estrogen deprivation syndrome which includes administering to a mammal in need thereof an effective amount of a compound of formula I and a compound of formula II:

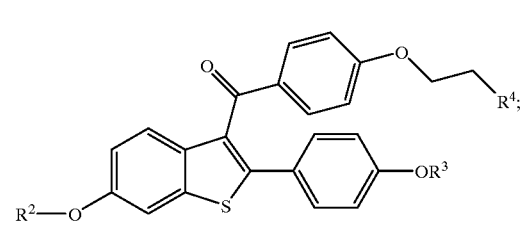

where:
$R^2$ and $R^3$ are independently hydrogen, $C_1$–$C_6$ alkyl, $CO(C_1$–$C_6$ alkyl), or COAr;
$R^4$ is pyrolidin-1-yl, piperidin-1-yl, or hexamethyleneimin-1-yl;

where the nitrogen of the R⁴ group is optionally the N-oxide; or a pharmaceutical salt or solvate thereof.

Furthermore, the present invention concerns pharmaceutical formulations, comprising a compound of formula I, or compounds of formula I and II, and pharmaceutical excipients, diluents, or carriers.

DETAILED DESCRIPTION OF THE INVENTION

General terms used in the description of compounds, methods, and formulations herein bear their usual meanings. For example, "$C_1$–$C_4$ alkyl" refers to methyl, ethyl, propyl, iso-propyl, cyclopropyl, n-butyl, s-butyl, t-butyl, and cyclobutyl. The term "$C_1$–$C_6$ alkyl" encompasses those listed for $C_1$–$C_4$ alkyl in addition to monovalent, straight, branched, or cyclic aliphatic chains of 5 or 6 carbon atoms including pentyl, cyclopentyl, hexyl, 2-methyl pentyl, cyclohexyl, and the like. The term "$C_1$–$C_4$ alkoxy" refers to methoxy, ethoxy, n-propoxy, iso-propoxy, cyclopropoxy, n-butoxy, s-butoxy, t-butoxy, and cyclobutoxy. The term "$C_1$–$C_6$ alkoxy" encompasses those listed for $C_1$–$C_4$ alkoxy in addition to straight, branched, or cyclic aliphatic chains of 5 or 6 carbon atoms which are attached through a monovalent oxygen atom and include but are not limited to, pentoxy, cyclopentoxy, hexoxy, 2-methylpentoxy, cyclohexoxy, and the like.

The term "halide" refers to chloride, bromide, or iodide.

The term "substituted phenyl" refers to a phenyl group having one to three substituents selected from the group consisting of $C_1$–$C_6$ alkyl, $C_1$–$C_4$ alkoxy, hydroxy, nitro, chloro, fluoro, or tri(chloro or fluoro)methyl.

Although the free-base form of formula II compounds can be used in the methods of the present invention, it is preferred to prepare and use a pharmaceutical salt form. Typical pharmaceutical salts include those salts prepared by reaction of the compounds of formula II with a mineral or organic acid. Such salts are known as acid addition salts. Thus, the term "pharmaceutical salt" refers to acid addition salts of a compound of formula II which are substantially non-toxic at the doses administered and are commonly known in the pharmaceutical literature. See e.g. Berge, S. M, Bighley, L. D., and Monkhouse, D. C., *J. Pharm. Sci.*, 66, 1, 1977. The pharmaceutical salts generally have enhanced solubility characteristics compared to the compound from which they are derived, and thus are often more amenable for use in pharmaceutical formulations.

Examples of pharmaceutical salts are the iodide, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, g-hydroxybutyrate, b-hydroxybutyrate, butyne-1,4-dioate, hexyne-1,4-dioate, hexyne-l, 6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like of a compound of formula II.

The term "solvate" represents an aggregate that comprises one or more molecules of the solute, such as a compound of formula I or II, with one or more molecules of solvent. Such solvent molecules would be those commonly used in the pharmaceutical literature, which are known to be non-detrimental to the recipient, e.g., water and ethanol.

The term "thermodynamic base" refers to a base which provides a reversible deprotonation of an acidic substrate, or is employed as a proton trap when a proton is a byproduct of a reaction, and is reactive enough to effect the desired reaction without significantly effecting any undesired reactions. Examples of thermodynamic bases include, but are not limited to, carbonates, bicarbonates, and hydroxides (e.g. lithium, sodium, or potassium carbonate, bicarbonate, or hydroxide), tri-($C_1$–$C_4$ alkyl)amines, or aromatic nitrogen containing heterocycles (e.g. pyridine).

The term "estrogen deprivation syndrome" contemplates those pathologies and conditions brought about by the loss of ovarian function (either natural, surgically, or chemically induced) and specifically to the loss of the ovarian hormones, especially estrogen. Since loss of estrogen is causative for the symptoms of the syndrome, each of those symptoms responds to the replacement of the lost estrogen hormone through the administration of the compounds of the current invention. Thus, the compounds and methods of the current invention would be useful and beneficial in treating or preventing estrogen deficiency symptoms, which include but are not limited to the following: osteoporosis, hyperlipidemia, atherosclerosis, vasomotor abnormalities (hot flashes), auto-immune diseases, skin and hair abnormalities, cardiovascular disease and degeneration, dementia and Alzheimer's disease, depression, weight gain or loss, certain types and conditions of diabetes, inappropriate healing and tissue repair, vaginal atrophy, urinary incontinence, sequelae of abnormal regulation of estrogen controlled genes, intra alia. It should be recognized that not all patients being treated for estrogen deprivation syndrome symptoms will necessarily have all the various pathologies listed, supra, thus, the specific use of the compounds and methods of the current invention may vary depending on the idiosyncratic nature and severity of those symptoms.

The terms "inhibit" or "inhibiting" mean prohibiting, treating, alleviating, ameliorating, halting, restraining, slowing or reversing the progression, or reducing the severity of a pathological symptom related to or resultant from estrogen deprivation syndrome. As such, these methods include both medical therapeutic (acute) and/or prophylactic (prevention) administration as appropriate.

As used herein, the term "effective amount" means an amount of compound or compounds of the present invention which is capable of inhibiting the symptoms of the various pathological conditions and symptoms, herein described.

By "pharmaceutical formulation," "pharmaceutical carrier," "pharmaceutical diluent," and "pharmaceutical excipient" it is meant that in a formulation containing a compound of formula I or a formulation containing a combination of a compound of formula I and II, the carrier, diluent, excipients, and salt are compatible with the other ingredients of the formulation, and not deleterious to the recipient thereof.

While all of the compounds of the present invention are useful, certain of the compounds are particularly interesting and are preferred. For example, compounds of formula I where R and R¹ are independently hydroxy or methoxy are preferred. The compound of formula I where R and R¹ are both hydroxy, i.e. 2-(4-hydroxyphenyl)-6-hydroxybenzo[b]thiophene, is most preferred. In addition, the hydrochloride salt of the compound of formula II where R² and R³ are both hydrogen, and R⁴ is piperidin-1-yl is also particularly preferred. This compound of formula II is [2-(4-hydroxyphenyl)-6- hydroxybenzo[b]thien-3-yl][4-[2-(1-piperidinyl)ethoxy]phenyl]methanone hydrochloride i.e. Raloxifene hydrochloride.

While all the formulations and methods employing a combination of a compound of formula I and II are useful, the possible combinations employing the preferred compounds listed above are particularly interesting and preferred. Most preferred is the combination of 2-(4-hydroxyphenyl)-6-hydroxybenzo[b]thiophene and Raloxifene hydrochloride.

The compounds of formula I may be prepared from compounds of formula III and IV as illustrated in Scheme 1 below where R and R¹ are as described supra.

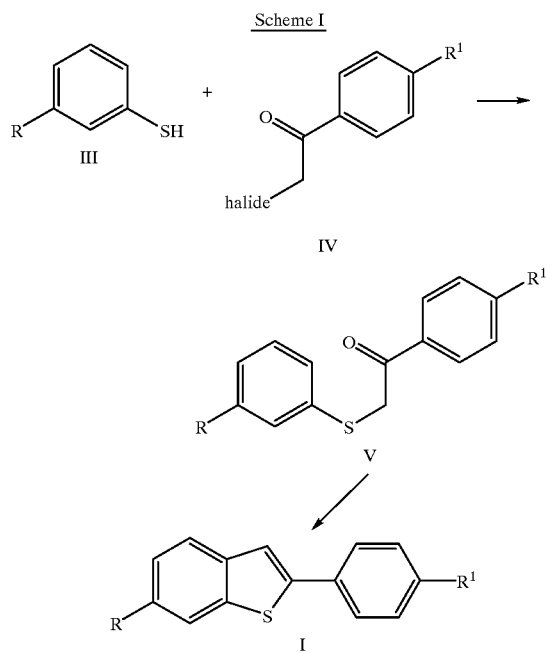

Compounds of formula III may be S-alkylated with a phenacyl halide of formula IV. Such S-alkylations are carried out in a solvent in the presence of a thermodynamic base at temperatures between 0° C. and 100° C. for one to twenty-four hours. A preferred solvent and base are typically ethanol and potassium hydroxide respectively. The reaction is preferably performed at ambient temperature for one to three hours. A preferred halide for the compound of formula IV is bromide.

The resulting compounds of formula V are cyclized to the compounds of formula I by treatment with an acid in a suitable solvent at a temperature between 50° C. and 200° C. for one to twenty-four hours. A preferred solvent and acid is polyphosphoric acid.

When R and/or R¹ is to be hydroxy, it is preferred that the above sequence be performed with a compound of formula III and/or IV where R and/or R¹ is $C_1$–$C_6$ alkoxy, OCH₂Ar, OCO($C_1$–$C_6$ alkyl), or OCOAr. The compounds of formula I where R and/or R¹ are hydroxy may then be prepared after the cyclization step by removing the $C_1$–$C_6$ alkyl, CH₂Ar, CO($C_1$–$C_6$ alkyl), or COAr moieties (protecting groups) from the resulting compounds of formula I. Methods for removing these protecting groups may be found in the Examples section which follows or in Chapter 2 of "Protective Groups in Organic Synthesis, 2nd Edition, T. H. Greene, et al., John Wiley & Sons, New York, 1991.

Compounds of formula I where R and R¹ are not hydrogen and only one of R or R¹ is hydroxy, may be prepared from compounds of formula I where R and R¹ are independently and differently $C_1$–$C_6$ alkoxy, OCH₂Ar, OCO($C_1$–$C_6$ alkyl), or OCOAr by removing selectively one of the protecting groups. Protecting groups which facilitate a selective removal and methods for the selective removal of one protecting group over the other are well known in the art. One example where selective removal is possible is where one protecting group is benzyl and the other is $C_1$–$C_4$ alkyl. The benzyl group may be removed selectively by catalytic hydrogenation. For further instruction on selective removal of these protecting groups see the Examples section which follows and the Greene reference cited above.

For further instruction on the preparation of compounds of formula I see U.S. Patent Nos. 4,133,814 and 4,418,068 and the publication, Jones, C. D., et al., *J. Med. Chem.*, 27, pp. 1057-1066 (1984), the teachings of which each are herein incorporated by reference.

The compounds of formula II which are not N-oxides, and their pharmaceutical salts, may also be prepared as taught in the previously incorporated U.S. patents and also as taught in U.S. Pat. Nos. 5,393,763 and 5,629,425, and PCT publication #US97/04259, the teachings of which each are herein incorporated by reference.

The compounds of formula II which are N-oxides may be prepared by dissolving or suspending a compound of formula II which is not an N-oxide in dilute aqueous solutions of hydrogen peroxide with a co-solvent such as methanol or ethanol. Reaction conditions for this reaction may range from ambient temperature to 100° C. and in duration from 24 to 72 hours. It should be noted that care must be taken in selecting the oxidizing agent and that many commonly used agents, e.g., chromic anhydride, potassium permanganate, and the like, capable of oxidizing the nitrogen can not be used, since they would also oxidize the sulfur of the benzo[b]thiophene. Thus, a milder agent such as hydrogen peroxide is preferred.

The optimal time for performing the reactions described herein can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. Intermediate and final products may be purified, if desired by common techniques such as recrystallization or chromatography over solid supports such as silica gel or alumina.

Compounds of formula III and IV are either commercially available or may be prepared by methods well known in the art.

The discussion of the synthesis is not intended to be limiting to the scope of the present invention, and should not be so construed. Application of the above chemistry enables the synthesis of the compounds of formula I, which includes, but is not limited to:

2-phenylbenzo[b]thiophene;
2-(4-hydroxyphenyl)benzo[b]thiophene;
2-(4-methoxyphenyl)benzo[b]thiophene;
2-(4-acetoxyphenyl)benzo[b]thiophene;
2-(4-benzoyloxyphenyl)benzo[b]thiophene;
2-(4-isopropoxyphenyl)benzo[b]thiophene;
2-phenyl-6-hydroxybenzo[b]thiophene;
2-phenyl-6-methoxybenzo[b]thiophene;
2-phenyl-6-isopropoxybenzo[b]thiophene;
2-phenyl-6-acetoxybenzo[b]thiophene;
2-phenyl-6-(4-methylbenzoyl)oxybenzo[b]thiophene;
2-(4-hydroxyphenyl)-6-hydroxybenzo[b]thiophene;
2-(4-methoxyphenyl)-6-methoxybenzo[b]thiophene;
2-(4-methoxyphenyl)-6-hydroxybenzo[b]thiophene;
2-(4-hydroxyphenyl)-6-methoxybenzo[b]thiophene;
2-(4-isopropoxyphenyl)-6-methoxybenzo[b]thiophene;
2-(4-isopropoxyphenyl)-6-hydroxybenzo[b]thiophene;
2-(4-methoxyphenyl)-6-isopropoxybenzo[b]thiophene;
2-(4-hydroxyphenyl)-6-isopropoxybenzo[b]thiophene;
2-(4-acetoxyphenyl)-6-acetoxybenzo[b]thiophene;
2-(4-methoxyphenyl)-6-acetoxybenzo[b]thiophene;
2-(4-acetoxyphenyl)-6-methoxybenzo[b]thiophene;
2-(4-acetoxyphenyl)-6-hydroxybenzo[b]thiophene;
2-(4-hydroxyphenyl)-6-acetoxybenzo[b]thiophene;
2-(4-benzoyloxyphenyl)-6-hydroxybenzo[b]thiophene;
2-(4-benzoyloxyphenyl)-6-enzoyloxybenzo[b]thiophene;
2-(4-cyclopentoxyphenyl)-6-hydroxybenzo[b]thiophene;
2-(4-hydroxyphenyl)-6-cyclopentoxybenzo[b]thiophene;
2-(4-cyclopentoxyphenyl)-6-cyclopentoxybenzo[b]thiophene;
2-(4-butoyloxyphenyl)-6-hydroxybenzo[b]thiophene;
2-(4-cyclopentoxyphenyl)-6-acetoxybenzo[b]thiophene; and the like.

Formulations and methods employing both a compound of formula I and II include, but are not limited to, the following combinations of the two compounds:

2-(4-methoxyphenyl)-6-methoxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-hydroxyphenyl)-6-methoxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-methoxyphenyl)-6-hydroxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-hydroxyphenyl)-6-hydroxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-methoxyphenyl)-6-methoxybenzo[b]thiophene and [2-(4-hydroxyphenyl)-6-hydroxybenzo[b]thien-3-yl][4-[2-(1-piperidinyl)ethoxy]phenyl]methanone N-oxide;

2-(4-hydroxyphenyl)-6-hydroxybenzo[b]thiophene and [2-(4-hydroxyphenyl)-6-hydroxybenzo[b]thien-3-yl][4-[2-(1-piperidinyl)ethoxy]phenyl]methanone N-oxide;

2-(4-methoxyphenyl)-6-methoxybenzo[b]thiophene and [2-(4-hydroxyphenyl)-6-hydroxybenzo[b]thien-3-yl][4-[2-(1-pyrolidinyl)ethoxy]phenyl]methanone hydrochloride;

2-(4-hydroxyphenyl)-6-hydroxybenzo[b]thiophene and [2-(4-hydroxyphenyl)-6-hydroxybenzo[b]thien-3-yl][4-[2-(1-pyrolidinyl)ethoxy]phenyl]methanone hydrochloride;

2-(4-methoxyphenyl)-6-hydroxybenzo[b]thiophene and [2-(4-methoxyphenyl)-6-hydroxybenzo[b]thien-3-yl][4-[2-(1-piperidinyl)ethoxy]phenyl]methanone hydrochloride;

2-(4-acetoxyphenyl)-6-acetoxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-cyclopentoxyphenyl)-6-methoxybenzo[b]thiophene and [2-(4-hydroxyphenyl)-6-hydroxybenzo[b]thien-3-yl][4-[2-(1-piperidinyl)ethoxy]phenyl]methanone hydrochloride;

2-(4-methoxyphenyl)-6-hydroxybenzo[b]thiophene and [2-(4-hydroxyphenyl)-6-hydroxybenzo[b]thien-3-yl][4-[2-(1-piperidinyl)ethoxy]phenyl]methanone N-oxide;

2-(4-hydroxyphenyl)-6-methoxybenzo[b]thiophene and [2-(4-hydroxyphenyl)-6-hydroxybenzo[b]thien-3-yl][4-[2-(1-piperidinyl)ethoxy]phenyl]methanone N-oxide; and the like.

The following Preparations and Examples further illustrate the synthesis of the compounds of the present invention. The examples are not intended to be limiting to the scope of the invention in any respect, and should not be so construed. The terms and abbreviations used in the instant preparations and examples have their normal meanings unless otherwise designated. For example "° C.", "N", "mmol", "g", "mL", "M", "HPLC", "mp", "EA", "MS", and "$^1$H-NMR", refer to degrees Celsius, normal or normality, millimole or millimoles, gram or grams, milliliter or milliliters, molar or molarity, high performance liquid chromatography, melting point, elemental analysis, mass spectrum, and proton nuclear magnetic resonance respectively.

Preparations

Preparation 1

2-(3-Methoxyphenylthio)-4'-Methoxyacetophenone

3-Methoxythiophenol (50.0 g, 0.356 mol) was dissolved in 700 mL of ethanol. To this mixture was added (20 g, 0.36 mol) of potassium hydroxide pellets. A total of (82.5 g, 0.36 mol) of 2-bromo-4'-methoxyacetophenone was added in small portions to keep the temperature of the reaction at approximately 25° C. The reaction was allowed to proceed at ambient temperature for three hours. The reaction was terminated by evaporation of the alcohol, which resulted in obtaining a brown oil. The oil was partitioned between 2 L of water and 1.5 L of diethylether. The ether layer was separated and washed with water, dried with anhydrous magnesium sulfate, and evaporated to a solid. The solid was crystallized from a mixture of diethylether-petroleum ether (3:1) to yield 78.5 g of the title compound as a pink crystalline solid. mp 53° C.–54° C. EA calculated for $C_{16}H_{16}O_3S$: C, 66.64; H, 5.59; O, 16.64; S, 11.12. Found: C, 66.55; H, 5.87; O, 16.82; S, 10.86.

Preparation 2

2-Phenylthioacetophenone

Thiophenol and 2-bromoacetophenone were converted to the title compound by the procedure of Preparation 1. mp 52° C.–53° C. EA calculated for $C_{14}H_{12}OS$: C, 73.65; H, 5.30; O, 7.01; S, 14.04. Found: C, 73.46; H, 5.50; O, 7.25; S, 14.30.

Preparation 3

2-Phenylthio-4'-Methoxyacetophenone

Thiophenol and 2-bromo-4'-methoxyacetophenone were converted to the title compound by the procedure of Preparation 1. mp 83° C.–85° C. EA calculated for $C_{15}H_{14}O_2S$: C, 69.74; H, 5.46. Found: C, 69.52; H, 5.48.

Preparation 4

2-(3-Isopropoxyphenyl)-4'-Methoxyacetophenone

3-Isopropoxythiophenol and 2-bromo-4'-methoxyacetophenone were converted to the title compound by the procedure of Preparation 1.

EXAMPLES

Example 1

2-(4-Methoxyphenyl)-6-Methoxybenzo[b]thiophene 2-(3-Methoxyphenylthio)-4-methoxyacetophenone (50 g, 0.173 mol) was added to 250 g of polyphosphoric acid at 95° C. The mixture was stirred and the temperature rose to 120° C. and ice was cautiously added. As the temperature rose to 130° C., after 30 minutes, additional ice was added and crystals of the product began to appear. Water was added to the reaction mixture and the product collected by filtration. The final product was recrystallized from ethyl acetate to give 30 g of the title compound. mp 193° C.–194° C. EA calculated for $C_{16}H_{14}O_2S$: C, 71.08; H, 5.22; O, 11.84; S, 11.86. Found: C, 71.03; H, 5.30; O, 11.81; S, 11.60.

Example 2

2-(4-Hydroxyphenyl)-6-Hydroxybenzo[b]thiophene 2-(4-Methoxyphenyl)-6-methoxybenzo[b]thiophene (10 g, 35.5 mmol) was suspended in 50 mL of 48% aqueous hydrobromic acid and 100 mL of glacial acetic acid. The reaction was heated to reflux under a nitrogen atmosphere for 120 hours. The reaction was allowed to cool and filtered. The solid product was washed with water and dried to yield 6.46 g of the title compound. $^1$H NMR: ($CDCl_3$-$d^6DMSO$):δ 7.54 (d, 1H), 7.48 (d, 2H), 7.27 (s, 1H), 7.24 (m, 1H), 6.92 (d, 1H), 6.85 (d, 2H). MS(FD): m/e=242 (M$^+$).

Example 3

2-(4-Acetoxyphenyl)-6-Acetoxybenzo[b]thiophene 2-(4-Hydroxyphenyl)-6-hydroxybenzo[b]thiophene (2.42 g, 10 mmol) was dissolved in 100 mL of tetrahydrofuran and triethylamine (8 g, 100 mmol) was added. The reaction mixture was stirred under a nitrogen atmosphere at ambient temperature, while acetylchloride (2 g, 30 mmol) was slowly added. After sixteen hours, the reaction was terminated by the addition of water. The product began to crystallize at the interface, the water layer was discarded, and product crystallized out of the tetrahydrofuran layer. The product was filtered off and dried to give 2.06 of the title compound. $^1$H NMR: ($d^6$-DMSO)δ 7.86 (s, 1H) 7.85 (d, 1H), 7.83 (s, 1H), 7.81 (d, 1H), 8.70 (d, 2H), 7.25 (d, 2H), 7.18 (dd, 1H). EA calculated for $C_{18}H_{14}O_4S$: C, 66.24; H, 4.32 Found: C, 66.14; H, 4.38. MS(FD): m/e=326 (M$^+$).

Example 4

2-(4-Benzoyloxyphenyl)-6-Benzoyloxybenzo[b]thiophene 2-(4-Hydroxyphenyl)-6-hydroxybenzo[b]thiophene and benzoyl chloride were converted to the title compound by the procedure of Example 3 to yield a white crystalline solid. mp 216° C.–218° C.

Example 5

2-Phenylbenzo[b]thiophene

2-Phenylthioacetophenone (63.8 g) was added to 450 g of polyphosphoric acid at 100° C. and then heated further to 190° C. for three hours. The reaction was allowed to cool below 100° C. before pouring it into a mixture of ice and water. The aqueous solution was extracted with ether. The ether layer was dried with magnesium sulfate and evaporated to yield a tan, amorphous solid. The residue was crystallized from acetone-ethanol to give 35.2 g of the title compound. mp 171° C.–172° C.

Example 6

2-(4-Methoxyphenyl)benzo[b]thiophene

2-Phenylthio-4'-methoxyacetophenone was converted to the title compound by the procedure of Example 2. mp 188° C.–190° C. EA calculated for $C_{15}H_{12}OS$: C, 74.97; H, 5.03; O, 6.66 Found: C, 74.69; H, 5.19; O, 6.75.

Example 7

2-(4-Methoxyphenyl)-6-Isopropoxybenzo[b]thiophene 2-(3-Isopropoxyphenylthio)-4'-methoxyacetophenone was converted to the title compound by the procedure of Example 2.

Example 8

2-(4-Methoxyphenyl)-6-Hydroxybenzo[b]thiophene 2-(4-Methoxyphenyl)-6-isopropoxybenzo[b]thiophene (1.0 g, 3.35 mmol) was dissolved in 10 mL of methylene chloride and warmed to 30° C. Boron trichloride (3.685 35 mL, 3.685 mmol 1M in methylene chloride) was slowly added to the stirring reaction solution. The reaction was allowed to proceed for one hour at ambient temperature. The reaction was quenched with the dropwise addition of methanol (0.536 g, 16.75 mmol). The reaction was stirred for two hours and a white precipitate formed. The solid as filtered off, washed three times with 10 mL portions of methylene chloride and dried to yield the title compound as a white solid. EA calculated for $C_{15}H_{12}O_2S$: C, 70.29; H, 4.72; S, 12.51. Found: C, 67.69; H, 4.65; S, 12.02. MS(FD): m/e= 256 (M$^+$).

The examples given below demonstrating the utility of the current invention are given for the purpose of illustration and should not be considered limiting in any way. The experimental model used in this demonstration is a model developed to mimic two of the major pathologies associated with human estrogen deprivation, i.e., hyperlipidemia and osteoporosis.

General Procedure

Seventy-five day old female Sprague Dawley rats (weight range of 200 g to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection

After a one week acclimation period (two weeks post-OVX) daily dosing with test compound or 17-α-ethynyl estradiol is initiated. The doses are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $C_{O2}$, the uterus was removed through a midline incision, and a wet uterine weight was determined.

Hyperlipidemia (Cholesterol Analysis)

Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Representative compounds of the present invention reduced serum cholesterol compared to the ovariectomized control animals.

Osteoporosis

Following the General Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, representative compounds of the present invention and ethynyl estradiol (EE2) in 20% hydroxypropyl β-cyclodextrin are orally administered to test animals and demonstrate a positive result, i.e., a reduction in the loss of bone mineral density.

The specific dose of a compound of formula I will, of course, be determined by the particular circumstances surrounding the case. Similarly, the route of administration is a factor determined by the specifics of each case. Thus, the exact dose and route of administration are best determined by the attending physician A typical daily dose of a compound of formula I would contain a nontoxic dosage level of from about 0.001 mg to about 800 mg/day. Preferred daily doses generally will be from about 0.001 mg to about 60 mg/day. Such a dosage may be given as a single dose or may be divided into two or three separate doses per day as necessary.

As mentioned, supra, the compounds of formula I may be used with a compound of formula II. Again, the exact amounts of the two agents (formula I and II compounds) may vary depending the nature of the symptoms to be treated as well as the patient's medical status. In general, such combinations would include 0.001 mg to 60 mg of a compound of formula I and 1.0 to 120 mg of a compound of formula II. A preferred combination would be one comprising 0.001 to 1 mg of a compound of formula I and 59 to 59.999 mg of a compound of formula II. A more preferred combination would be one comprising 0.001 to 0.1 mg of a compound of formula I and 59.9 to 59.999 mg of a compound of formula II. An even more preferred combination would comprise 0.001 to 0.1 mg of a preferred compound of formula I (where R and $R^1$ are independently hydroxy or methoxy) and 59.9 to 59.999 mg of Raloxifene hydrochloride. Most preferred is the combination comprising 0.001 to 0.1 mg of the most preferred compound of formula I (where R and $R^1$ are both hydroxy) and 59.9 to 59.999 mg of Raloxifene hydrochloride.

The compounds of this invention can be administered by a variety of routes including oral, rectal, transdermal, buccal, aerosal, topical, opthalmic, subcutaneous, intravenous, intramuscular, intranasal, and the like. These compounds preferably are formulated prior to administration, the selection of which will be decided by the attending physician. Thus, another aspect of the present invention is a pharmaceutical formulation comprising an effective amount of a compound of Formula I or a pharmaceutical formulation comprising an effective amount of a compound of formula I and II, or a pharmaceutical salt thereof, and a pharmaceutical carrier, diluent, or excipient. The total active ingredients in such formulations comprises from 0.1% to 99.9% by weight of the formulation.

Pharmaceutical formulations of the present invention can be prepared by procedures known in the art using well known and readily available ingredients. For example, the compounds of formula I or the compounds of formula I and II can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Formulation Examples

The following formulation examples are illustrative only and are not intended to limit the scope of the present invention in any way.

Formulation 1: Gelatin Capsules

Hard gelatin capsules are prepared using the following:

| Ingredient | Quantity (mg/capsule) |
| --- | --- |
| Compound of formula I | 0.001–200 |
| Starch, NF | 0–650 |
| Starch flowable powder | 0–650 |
| Silicone fluid 350 centistokes | 0–15 |

The formulation above may be changed in compliance with the reasonable variations provided.

Formulation 2: Tablets

A tablet formulation is prepared using the ingredients below:

| Ingredient | Quantity (mg/tablet) |
| --- | --- |
| Compound of formula I | 0.001–200 |
| Cellulose, microcrystalline | 200–650 |
| Silicon dioxide, fumed | 10–650 |
| Stearate acid | 5–15 |

The components are blended and compressed to form tablets.

Formulation 3: Tablets

Tablets each containing 2.5-1000 mg of active ingredient are made up as follows:

| Ingredient | Quantity (mg/tablet) |
| --- | --- |
| Compound of formula I | 0.001–200 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Formulation 4: Suspensions

Suspensions each containing 0.1-1000 mg of medicament per 5 ml dose are made as follows:

| Ingredient | Quantity (mg/5 ml) |
| --- | --- |
| Compound of formula I | 0.001–200 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 5: Combination Tablets

| Ingredient | Quantity (mg/tablet) |
| --- | --- |
| Compound of formula I | 0.001–1 |
| Compound of Formula II | 59–59.999 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Formulation 5: Combination Tablets

| Ingredient | Quantity (mg/tablet) |
| --- | --- |
| A preferred compound of formula I | 0.001–0.1 |
| Raloxifene hydrochloride | 59–59.999 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

I claim:

1. A pharmaceutical formulation comprising a compound of formula I:

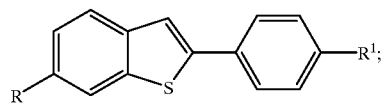

where:
R and $R^1$ are independently hydrogen, hydroxy, $C_1$–$C_6$ alkoxy, $OCH_2Ar$, $OCO(C_1$–$C_6$ alkyl), OCOAr; and
Ar is phenyl or substituted phenyl; or a solvate thereof; and a compound of formula II:

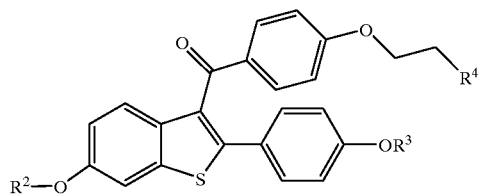

where:
$R^2$ and $R^3$ are independently hydrogen, $C_1$–$C_6$ alkyl, $CO(C_1$–$C_6$ alkyl), or COAr;
$R^4$ is pyrolidin-1-yl, piperidin-1-yl, or hexamethyleneimin-1-yl;
where the nitrogen of the $R^4$ group is optionally the N-oxide; or
a pharmaceutical salt or solvate thereof; and pharmaceutical carriers, excipients, or diluents.

2. A formulation according to claim 1 comprising 0.001 to 60 mg of a compound of formula I where R and $R^1$ are independently hydroxy or methoxy, or a solvate thereof, and 1 to 120 mg of a compound of formula II being raloxifene hydrochloride.

3. A formulation according to claim 2 wherein said compound of formula I is 2-(4-hydroxyphenyl)-6-hydroxybenzo[b]thiophene, or a solvate thereof.

4. A formulation according to claim 3 comprising 0.001 to 1 mg of the compound of formula I, or a solvate thereof, and 59 to 59.999 mg of raloxifene hydrochloride.

5. A formulation according to claim 4 comprising 0.001 to 0.1 mg of the compound of formula I, or a solvate thereof, and 59.1 to 59.999 mg of raloxifene hydrochloride.

6. A formulation according to claim 1 where the compound of formula I is a compound selected from the group consisting of: 2-phenylbenzo[b]thiophene; 2-(4-hydroxyphenyl)benzo[b]thiophene; 2-(4-methoxyphenyl)benzo[b]thiophene; 2-(4-acetoxyphenyl)benzo[b]thiophene; 2-(4-benzoyloxyphenyl)benzo[b]thiophene; 2-(4-isopropoxyphenyl)benzo[b]thiophene; 2-phenyl-6-hydroxybenzo[b]thiophene; 2-phenyl-6-methoxybenzo[b]thiophene; 2-phenyl-6- isopropoxybenzo[b]thiophene; 2-phenyl-6-(4-acetoxybenzo[b]thiophene; 2-phenyl-6-(4-methylbenzoyl)oxybenzo[b]thiophene; 2-(4-hydroxyphenyl)-6-hydroxybenzo[b]thiophene; 2-(4-methoxyphenyl)-6-methoxybenzo[b]thiophene; 2-(4-methoxyphenyl)-6-hydroxybenzo[b]thiophene; 2-(4-hydroxyphenyl)-6-methoxybenzo[b]thiophene; 2-(4-isopropoxyphenyl)-6-methoxybenzo[b]thiophene; 2-(4-isopropoxyphenyl)-6-hydroxybenzo[b]thiophene; 2-(4-methoxyphenyl)-6-isopropoxybenzo[b]thiophene; 2-(4-hydroxyphenyl)-6-isopropoxybenzo[b]thiophene; 2-(4-acetoxyphenyl)-6-acetoxybenzo[b]thiophene; 2-(4-methoxyphenyl)-6-acetoxybenzo[b]thiophene; 2-(4-acetoxyphenyl)-6-methoxybenzo[b]thiophene; 2-(4-acetoxyphenyl)-6-hydroxybenzo[b]thiophene; 2-(4-hydroxyphenyl)-6-acetoxybenzo[b]thiophene; 2-(4-benzoyloxyphenyl)-6-hydroxybenzo[b]thiophene; 2-(4-benzoyloxyphenyl)-6-benzoyloxybenzo[b]thiophene; 2-(4-cyclopentoxyphenyl)-6-hydroxybenzo[b]thiophene; 2-(4-hydroxyphenyl)-6-cyclopentoxybenzo[b]thiophene; 2-(4-cyclopentoxyphenyl)-6-cyclopentoxybenzo[b]thiophene; 2-(4-butoyloxyphenyl)-6-hydroxybenzo[b]thiophene; and 2-(4-cyclopentoxyphenyl)-6-acetoxybenzo[b]thiophene; or a solvate thereof.

7. A formulation according to claim 6 wherein said formula II compound is raloxifene hydrochloride.

8. An article of manufacture comprising packaging material and a pharmaceutical formulation contained within the packaging material, where the packaging material comprises a label which indicates the pharmaceutical formulation may be administered for inhibiting a pathology of estrogen deprivation syndrome, and where the pharmaceutical formulation comprises a compound of formula I(a):

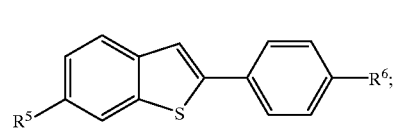

where:
$R^5$ and $R^6$ are independently hydroxy or methoxy; or a solvate thereof;
and a compound of the formula:

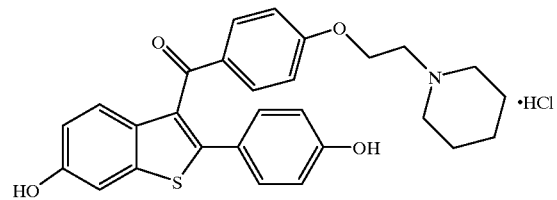

or a solvate thereof.

9. An article of manufacture according to claim 8 which comprises 0.001 to 1 mg of a compound of formula I(a), or a solvate thereof, and 59 to 59.999 mg of a compound of the formula:

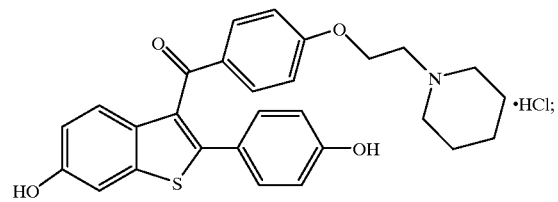

or a solvate thereof.

10. An article of manufacture according to claim 9 where the compound of formula I(a) is 2-(4-hydroxyphenyl)-6-hydroxybenzo [b]thiophene, or a solvate thereof.

11. An article of manufacture according to claim 10 wherein said pathology is osteoporosis.

* * * * *